United States Patent [19]

Ishibe et al.

[11] 4,309,301
[45] Jan. 5, 1982

[54] METHYLCHLOROFORM STABILIZER COMPOSITION EMPLOYING AN ALKYNYL SULFIDE

[75] Inventors: Nobuyuki Ishibe, Lake Jackson, Tex.; Thomas G. Metcalf, Albuquerque, N. Mex.

[73] Assignee: The Dow Chemical Company, Midland, Mich.

[21] Appl. No.: 221,945

[22] Filed: Dec. 31, 1980

[51] Int. Cl.$^3$ .................................................. C23G 5/02
[52] U.S. Cl. ..................................... 252/172; 252/162; 252/171; 252/364; 570/107; 570/120
[58] Field of Search ............... 252/171, 172, 162, 364; 570/107, 120

[56] References Cited

U.S. PATENT DOCUMENTS

| | | | |
|---|---|---|---|
| 2,838,458 | 6/1958 | Bachtel | 252/171 |
| 3,265,747 | 8/1966 | Cormany et al. | 252/171 X |
| 3,467,722 | 9/1969 | Archer et al. | 252/171 X |
| 3,475,503 | 10/1969 | Archer et al. | 252/171 X |
| 3,535,392 | 10/1970 | Cormany et al. | 252/171 X |
| 3,644,169 | 2/1972 | Crabb et al. | 252/171 X |
| 3,676,355 | 7/1972 | Vuillemenot | 252/171 X |
| 3,959,397 | 5/1976 | Richtzenhain et al. | 252/171 X |
| 4,189,397 | 2/1980 | Allen | 252/171 |

*Primary Examiner*—Mayer Weinblatt
*Attorney, Agent, or Firm*—A. C. Ancona

[57] ABSTRACT

An alkyl alkynyl sulfide can be employed to stabilizer methylchloroform against reaction with the common metals of construction. Stabilization is enhanced by combining with other known stabilizers. Nitroalkanes, alkyl nitrates or alkynols may be employed to eliminate the need of dioxane and alkylene oxides, while the use of the alkyl nitrates or alkynols eliminates the need for a nitroalkane in the stabilizer formulation.

9 Claims, No Drawings

METHYLCHLOROFORM STABILIZER COMPOSITION EMPLOYING AN ALKYNYL SULFIDE

BACKGROUND OF THE INVENTION

Numerous compounds, including ethers, cyclic ethers, alcohols, including aliphatic, olefinic and acetylenic varieties, nitroalkanes, esters, and others have been employed in various combinations to stabilize the chlorinated hydrocarbons in the presence of various metals.

Sulfur-containing compounds have also been employed as stabilizers for methylchloroform, e.g. mercaptans and disulfides have been used as secondary inhibitors (U.S. Pat. No. 3,641,169) to prevent the reaction of acids with the epoxides employed as stabilizers. Such acids are frequently found in metal cleaning operations. Sulfoxides have also been taught as useful in combination with epoxides (U.S. Pat. No. 3,535,392) as stabilizers for methylchloroform. Dithianes and thioxanes are taught to stabilize methylchloroform against reaction with iron and aluminum (U.S. Pat. No. 3,384,673). Other sulfur compounds are disclosed as useful stabilizers in U.S. Pat. Nos. 3,439,051 (dithiin); 3,467,722 (trimethylene sulfide); and U.S. Pat. No. 3,763,048 (1,3-dithiolane, 1,3-oxathiolane).

It has now been discovered that an alkyl alkynyl sulfide, especially methyl 2-propynyl sulfide, is useful alone or in combination with other inhibitors for stabilizing methylchloroform.

SUMMARY OF THE INVENTION

An alkyl alkynyl sulfide, in particular methyl 2-propynyl sulfide, is useful as an inhibitor against metal corrosion when used in methylchloroform which is in contact with metals. It is useful alone or its inhibitory power can be enhanced by its combination with other known inhibitors, especially nitroalkanes, isopropyl nitrate, or 2-methyl-3-butyn-2-ol.

DETAILED DESCRIPTION OF THE INVENTION

The use of an alkyl alkynyl sulfide when used in combination with an alkyl nitrate or an acetylenic alcohol can eliminate the need for dioxane, alkylene oxides, and nitroalkanes; while the use of a nitroalkane in combination with the alkyl alkynyl sulfide can eliminate the need for the dioxane and alkylene oxide components.

The alkyl alkynyl sulfide can be employed alone to stabilize methylchloroform and when so used should be present in a concentration of from about 2 to about 8 volume percent in the stabilized solvent. The preferred concentration is from about 3 to about 5 volume percent. The compounds useful as the stabilizer are methyl, ethyl and propyl 2-propynyl sulfides may be employed, the methyl compound being preferred.

When used in combination with another inhibitor, e.g. a nitroalkane, an alkyl nitrate or an acetylenic alcohol, the alkyl propynyl sulfide is employed at a concentration of from 1 to 5 percent and the other component at from 1 to 5 percent by volume based on the volume of the total of stabilizer and solvent.

The nitroalkanes and alkyl nitrates useful are those containing from one to three carbon atoms. Thus, methyl, ethyl, propyl and isopropyl nitrates are effective and nitromethane, nitroethane and nitropropanes may be employed. The acetylenic alcohols useful are those having from 3 to 5 carbon atoms, e.g. 2-propyn-1-ol, 3-butyn-1-ol, 2-butyn-1-ol, 1-methyl-3-butyn-1-ol, 2-methyl-3-butyn-1-ol, 1-methyl-2-propyn-1-ol, and the like.

The following examples are illustrative of the invention and are shown by comparison to analogous and similar stabilizer compounds.

EXAMPLES 1-6

Approximately 430 g of a 1,1,1-trichloroethane solution blended with methyl 2-propynyl sulfide singly or in combination with other stabilizers was partitioned by distillation into equal volume fractions. Ten ml aliquots of each fractionated top (T) and bottom (B) and unfractionated (U) solutions were refluxed for seven days in the presence of Al-2024, Zn, Cu, brass, steel, and Fe metals and the stability of the solution was rated by showing the number of hours during which no corrosion of the metals had occurred. Results are shown in Table I.

TABLE I

| Example No. | Stabilizer* Component | Vol. % | Metals** | Time (hrs) | Fraction |
|---|---|---|---|---|---|
| 1 | MPS | 3 | Al, Zn, Brass Zn pellets, Cu wire, Al chips | 168 | U |
| 2a | MPS | 4 | Al, Zn, Brass | | |
|  | NM | 0.4 | Al chips, Zn pellets | >168 | U |
|  | NE | 0.6 | Fe, Steel | | |
| b | Same | Same | Cu | 144 | U |
| c | Same | Same | Same | >168 | T |
| d | Same | Same | Al, Zn | | |
|  |  |  | Al chips, Zn pellets Steel wool, Fe filings | 168 | B |
| e | Same | Same | Cu, Brass | 144 | B |
| 3a | MPS | 4 | Al, Zn, | | |
|  | IPN | 2 | Al chips, Zn pellets Steel, Fe, Brass | >168 | U |
| b | Same | Same | Cu wire | 144 | U |
| c | Same | Same | Same | >168 | T |
| d | Same | Same | Al, Zn, Al chips, Zn pellets, steel, Fe | >168 | B |
| e | Same | Same | Cu, brass | 144 | B |
| 4a | MPS | 4 | Al, Zn, Al chips, | | |
|  | MBY | 2 | Zn pellets, Steel, Fe, Brass, Cu | >168 | U |
| b | Same | Same | All in 4a except Fe | >168 | T |
| c | Same | Same | Fe | 145 | T |
| d | Same | Same | All in 4a except steel | >168 | B |
| e | Same | Same | Steel | 95 | B |
| 5a | MPS | 3 | Al, Brass | >168 | U |
|  | AcN | 1 | | | |
| b | Same | Same | Zn | 6 | U |
| 6a | MPS | 3 | Al, Brass | >168 | U |
|  | TAA | 1 | | | |
| b | Same | Same | Zn | 5 | U |
| 7 | MPS | 1 | Al, Zn, Brass | >168 | U |
|  | IPN | 3 | Steel, Fe, | | B |
|  | NM | 0.4 | Al, Cu, Brass, Steel | >168 | T |
|  | NE | 0.6 | Zn | 144 | T |

*MPS = methyl-2-propynyl sulfide, NM = nitromethane, NE = nitroethane, IPN = isopropyl nitrate, MBY = 2-methyl-3-butyn-2-ol, AcN = acetonitrile, TAA = t-amyl alcohol,
**When not otherwise indicated Al, Zn and brass were employed in the form of coupons; steel employed as wool, Fe as filings and Cu as wire. Aluminum employed was Al-2024 as both coupons and chips.

COMPARATIVE EXAMPLE A

In a comparison test the analog of MPS, methyl propynyl ether, was employed at 3 volume % against aluminum, zinc and brass. The unfractionated material provided protection to the extent of 7, 24 and 46 hours, respectively.

EXAMPLE 8

A test to simulate a two-chamber vapor degreaser was carried out in a glass apparatus in which a 500 ml round-bottom flask (sump) was connected by a tilted side arm with a 500-ml round-bottom flask (dip) equipped with a condenser. Five hundred ml of a methylchloroform solution formulated with 4 vol. % methyl 2-propynyl sulfide and 2 vol. % i-propyl nitrate were added to the dip, half of the solution (250 ml) overflowing into the sump. The sump solution was gently boiled and the dip was kept warm at 68–70° C. The vapor was condensed into the warm dip flask from which excess solution was returned into the boiling sump solution. After the solution was refluxed for 2 days, 13.5 ml of mineral oil was added to the sump flask. The mixture was refluxed for 2 days and, then, the mixture of the following metals was added to the sump and dip. Metal additions to the sump and dip included 1.5 g of Al-2024 chips, 0.5 g of steel wool, 3.5 g of mossy Zn (only 2.1 g of mossy Zn for the dip), and 3.5 g of 70/30 brass chips. The mixture was refluxed for 7 days. No metal corrosion and discoloration of the dip solution was observed, whereas the sump solution turned reddish brown. The dip and sump solutions were then employed in 7-day reflux tests as in Examples 1–7. Results of tests with metals are shown in Table II.

TABLE II

| Sample Solution | Metal | Rating* |
| --- | --- | --- |
| dip | Al-1100 chips | 0 |
|  | Al-2024 chips | 1 |
|  | mossy zinc | 0 |
|  | brass chips | 0 |
|  | iron filings | 0 |
| sump | Al-1100 chips | 0 |
|  | Al2024 chips | 0 |
|  | mossy zinc | 0 |
|  | brass chips | 0 |
|  | iron filings | 0 |

*Rating 0 means no corrosion and no discoloration after 7-day reflux. A Rating of 5 indicates extensive corrosion and/or discoloration.

We claim:

1. A stabilized methylchloroform composition consisting essentially of methylchloroform and an alkyl 2-propynyl sulfide, wherein the alkyl group contains from 1–3 carbon atoms and the alkyl 2-propynyl sulfide is present in a concentration of from about 2 to about 8 volume percent.

2. The composition of claim 1 wherein the alkyl 2-propynyl sulfide is present in a concentration of from about 3 to about 5 volume percent.

3. The composition of claim 1 wherein the composition contains a second stabilizer selected from the group consisting of a nitroalkane having from 1 to 3 carbon atoms, an alkyl nitrate having from 1 to 3 carbon atoms and an acetylenic alcohol having from 3 to 5 carbon atoms and wherein the alkyl propynyl sulfide is present in an amount of from about 1 to about 5 percent and the second stabilizer is present in an amount of from about 1 to about 5 percent based on the total volume of the composition.

4. The composition of claim 3 wherein the alkyl propynyl sulfide is methyl-2-propynyl sulfide, and the second stabilizer is 2-methyl-3-butyn-2-ol.

5. The composition of claim 3 wherein the alkyl propynyl sulfide is methyl-2-propynyl sulfide, and the second stabilizer is nitromethane or nitroethane.

6. A method of stabilizing methylchloroform against attack by metals in contact therewith consisting essentially of blending with said methylchloroform as the stabilizer a lower alkyl-2-propynyl sulfide, prior to placing said metals in contact with said methylchloroform.

7. The method of claim 6 wherein the lower alkyl group of the stabilizer contains from 1 to 3 carbon atoms.

8. The method of claim 7 wherein the lower alkyl-2-propynyl sulfide is methyl-2-propynyl sulfide.

9. The method of claim 8 wherein a second stabilizer selected from the group consisting of a nitroalkane, an alkyl nitrate, and an acetylenic alcohol is blended therewith.

* * * * *